(12) United States Patent
Chung et al.

(10) Patent No.: US 10,061,893 B2
(45) Date of Patent: Aug. 28, 2018

(54) METHOD AND APPARATUS FOR CONTROLLING ELECTRONIC MEDICAL RECORD SYSTEM BASED OUTPUT WINDOW

(71) Applicant: SEOUL NATIONAL UNIVERSITY BUNDANG HOSPITAL, Gyeonggi-do (KR)

(72) Inventors: Chin Youb Chung, Gyeonggi-do (KR); Rong Min Baek, Seoul (KR); Hee Hwang, Daejeon (KR); Kee Hyuck Lee, Gyeonggi-do (KR); Soo Young Yoo, Gyeonggi-do (KR); Jong Hoar Yoon, Gyeonggi-do (KR); Yeon Soo Hwang, Gyeonggi-do (KR); Eun Young Cho, Gyeonggi-do (KR); Hyun Young Baek, Gyeonggi-di (KR)

(73) Assignee: SEOUL NATIONAL UNIVERSITY BUNDANG HOSPITAL, Gyeonggi-Do (KR)

( * ) Notice: Subject to any disclaimer, the term of this patent is extended or adjusted under 35 U.S.C. 154(b) by 476 days.

(21) Appl. No.: 14/773,150

(22) PCT Filed: Feb. 27, 2014

(86) PCT No.: PCT/KR2014/001647
§ 371 (c)(1),
(2) Date: Sep. 4, 2015

(87) PCT Pub. No.: WO2014/137106
PCT Pub. Date: Sep. 12, 2014

(65) Prior Publication Data
US 2016/0012188 A1    Jan. 14, 2016

(30) Foreign Application Priority Data
Mar. 4, 2013    (KR) .................. 10-2013-0022901

(51) Int. Cl.
*G06F 3/048* (2013.01)
*G06F 19/00* (2018.01)
(Continued)

(52) U.S. Cl.
CPC .......... *G06F 19/324* (2013.01); *G06F 3/0481* (2013.01); *G06F 3/0482* (2013.01);
(Continued)

(58) Field of Classification Search
CPC .. G06F 3/04883; G06F 3/0482; G06F 3/0481; G06F 3/0488; G06F 3/04886;
(Continued)

(56) References Cited

U.S. PATENT DOCUMENTS

2005/0160376 A1* 7/2005 Sciammarella ....... G06F 3/0481
                                                                   715/838
2006/0224992 A1    10/2006 Rossi et al.
(Continued)

FOREIGN PATENT DOCUMENTS

JP        05250126 A      9/1993
JP      2009031863 A      2/2009
(Continued)

OTHER PUBLICATIONS

Office action dated Oct. 18, 2016 from Australian Patent Office in a counterpart Australian Patent Application No. 2014226774.
(Continued)

*Primary Examiner* — Di Xiao
(74) *Attorney, Agent, or Firm* — The PL Law Group, PLLC (57) ABSTRACT

The present invention provides a method of controlling an EMR system-based output window, including: when a window size setting mode configured to set sizes for respective windows displayed on an EMR screen is executed, successively displaying a plurality of windows in a preset size;
(Continued)

when a user interrupt has occurred for any one of the displayed windows, activating the corresponding window, and enlarging the size of the window based on a stepwise variable range for an output window; determining locations by controlling the sizes of the respective windows successively displayed on the EMR screen in response to the size of the window enlarged based on the stepwise variable range; when a window different from the windows successively displayed upon the window size setting mode is called, listing the successively displayed windows, displaying the listed windows in a predetermined region, and displaying the called window in a preset size.

9 Claims, 6 Drawing Sheets

(51) Int. Cl.
  *G06F 3/0481* (2013.01)
  *G06Q 50/24* (2012.01)
  *G06F 3/0482* (2013.01)
  *G06F 3/0484* (2013.01)
  *G16H 10/60* (2018.01)
(52) U.S. Cl.
  CPC ........... *G06F 3/0484* (2013.01); *G06Q 50/24* (2013.01); *G16H 10/60* (2018.01)
(58) Field of Classification Search
  CPC ............ G06F 3/04845; G06F 3/04817; G06F 2203/04803; G06F 3/0485; G06F 9/4443; G06F 2203/04806; G06F 3/04842; G06F 2203/04808; G06F 3/0486; G06F 3/0483; G06F 3/0484; G06F 3/0416; G06F 3/048; G06F 17/212
  USPC ......................................... 715/803, 790, 792
  See application file for complete search history.

(56) References Cited

U.S. PATENT DOCUMENTS

2009/0031248 A1  1/2009  Kano et al.
2010/0083164 A1* 4/2010  Martin ................... G16H 40/63
                                              715/781
2011/0175930 A1* 7/2011  Hwang ................. G06F 3/0481
                                              345/629

FOREIGN PATENT DOCUMENTS

JP   2009031864 A    2/2009
KR   10-2007-0116594 A   12/2007
KR   10-2007-0117166 A   12/2007

OTHER PUBLICATIONS

Office action dated Jul. 1, 2016 from Australian Patent Office in a counterpart Australian Patent Application No. 2014226774.
International Search Report for PCT/KR2014/001647.

* cited by examiner

METHOD AND APPARATUS FOR CONTROLLING ELECTRONIC MEDICAL RECORD SYSTEM BASED OUTPUT WINDOW

TECHNICAL FIELD

The present invention relates to an electronic medical record system, and more particularly to a method and apparatus for controlling an EMR (Electronic Medical Record) system-based output window, which enlarge the size of a window, for which a user interrupt has occurred, based on a stepwise variable range on an EMR screen in which a plurality of windows are successively displayed in a preset size, reduce or list the remaining windows by controlling the sizes of the respective remaining windows in response to the enlarged window, and display the windows on a single screen.

BACKGROUND ART

A method of computerizing all medical information generated in a hospital without change by combining a conventional medical recording method of managing records using paper charts with IT technology is referred to as an Electronic Medical Record (EMR) method. This EMR method refers to a method of recording all types of medical information generated during the diagnosis and treatment of each patient, for example, health status, a medical history, examination results, prescription results, drug reactions, hospitalization records, etc. for each patient, in a specific database.

The EMR method is preferable in terms of the enhancement of hospital competitiveness, the improvement of a medical environment, and the acquisition of clinical research data. That is, the understanding of hospital administration status and the efficient use of personal resources can be achieved by the construction of an automated system, customized medical service can be provided by tracking the medical history of an individual, and clinical data can be used in various fields by accumulating the clinical data. The EMR method also has the advantages of improving work efficiency, improving communication between medical staff members, and preventing medical mistakes.

Meanwhile, when a medical staff member desires to retrieve the examination results of a patient in such an EMR system, the member can retrieve the examination results only if the member must move to a main screen for each medical treatment support department (a laboratory medical examination, imaging examination, function examination, or pathology examination department or the like) via a main EMR screen, input a patient number and a search period, and then perform a search. That is, in order to retrieve the results of a desired specific examination, a medical staff member must move to a screen for a corresponding examination department and then perform a search on each screen. Furthermore, the EMR system does not support the function of comparing the examination results of various departments on a single screen.

DISCLOSURE

Technical Problem

The present invention is intended to provide technology that is capable of preventing inconvenience in which, in order to retrieve examination results for each patient, a medical staff member must switch a screen from a main EMR screen to a main screen for each examination department, which provides data on each of a plurality of examination results, and then perform a search on the corresponding screen.

Technical Solution

In accordance with an aspect of the present invention, there is provided a method of controlling an EMR system-based output window, including: when a window size setting mode configured to set sizes for respective windows displayed on an EMR screen is executed, successively displaying a plurality of windows in a preset size; when a user interrupt has occurred for any one of the displayed windows, activating the corresponding window, and enlarging the size of the window based on a stepwise variable range for an output window; determining locations by controlling the sizes of the respective windows successively displayed on the EMR screen in response to the size of the window enlarged based on the stepwise variable range; when a window different from the windows successively displayed upon the window size setting mode is called, listing the successively displayed windows, displaying the listed windows in a predetermined region, and displaying the called window in a preset size.

In accordance with another aspect of the present invention, there is provided an apparatus for controlling an EMR system-based output window, including: a user interface unit configured to receive a user interrupt and a user gesture; and a control unit configured to successively display a plurality of windows in a preset size on an EMR screen according to a window size setting mode; when a user interrupt has occurred for any one of the displayed windows, activates the corresponding window, enlarges a size of the window based on a stepwise variable range for an output window, and determines locations by controlling the sizes of the other successively displayed windows in response to the size of the enlarged window; and when a new window is called, lists the successively displayed windows, displays the listed windows in a predetermined region, and displays the called window in a preset size.

Advantageous Effects

The present invention has the effects of preventing inconvenience in which, in order to retrieve examination results for each patient, a medical staff member must switch a screen from a main EMR screen to a main screen for each medical department and then perform a search on the corresponding screen, and the effect of displaying a large amount of data via framed individual windows in a distinctive manner and enabling data item-based retrieval and searching within a single screen.

MODE FOR INVENTION

Preferred embodiments according to the present invention will be described in detail below with reference to the accompanying drawings. In the following description, specific details, such as specific components, etc., are described. However, these specific details are provided merely to help a more fully understanding of the present invention, and it will be apparent to those having ordinary knowledge in the art that these specific details may be subjected to predetermined modifications or variations without departing from the scope of the present invention.

The present invention relates to an EMR system, and more particularly to a technology, which enlarges the size of a window, for which a user interrupt has occurred, based on a stepwise variable range on an EMR screen in which a plurality of windows are successively displayed in a preset size, reduces or lists the remaining windows by controlling the sizes of the respective remaining windows in response to the enlarged window, displays the windows, and, when a new window is called, lists the windows displayed on the EMR screen in the form of a list on one side of the EMR screen, and displays the called window in a preset size.

Furthermore, the present invention is intended to provide technology that groups the items of a list, within a specific service function supported by an EMR system, into a preset number of groups, generates segment blocks in accordance with the respective grouped items, displays the items in the respective blocks, and, when items of a subsequent group are sequentially called on a unit item basis, displays each called unit item in a segment block region at a first location, sequentially displays the item displayed in the segment block region at the first location and items displayed in respective blocks at locations different from the segment block region at the first location in subsequent adjacent segment block regions, and deletes an item displayed in the lowest segment block region, thereby preventing inconvenience in which in order to retrieve status information for each patient, a medical staff member must switch a screen from a main EMR screen to a main screen for each treatment department and then perform a search on the corresponding screen, and also enabling data item-based retrieval and search within a single screen by displaying a large amount of data in framed individual windows in a distinctive manner.

Furthermore, although the examination result provision technology to which the present invention has been applied is technology that can be applied to all types of search systems between a server and clients that operate in conjunction with one another over a network, the following detailed description of the present invention is given with a focus on an EMR system in a hospital by way of example.

Furthermore, in the detailed description of the present invention, the term "user interrupt" used herein refers to a user's intention to perform input via a screen on which a window has been displayed, and refers to pointing intended to select or activate a target, i.e., a window in the present invention, using an input means, such as a mouse, touch pen or finger. Furthermore, the term "user gesture" includes a drag, i.e., the operation of pressing a point of a window and then dragging the point to another location without releasing it in order to select or activate a window via a user interface unit.

A method of controlling an EMR system-based output window according to an embodiment of the present invention is described in detail below with reference to FIGS. 1 to 5.

Figure 1:
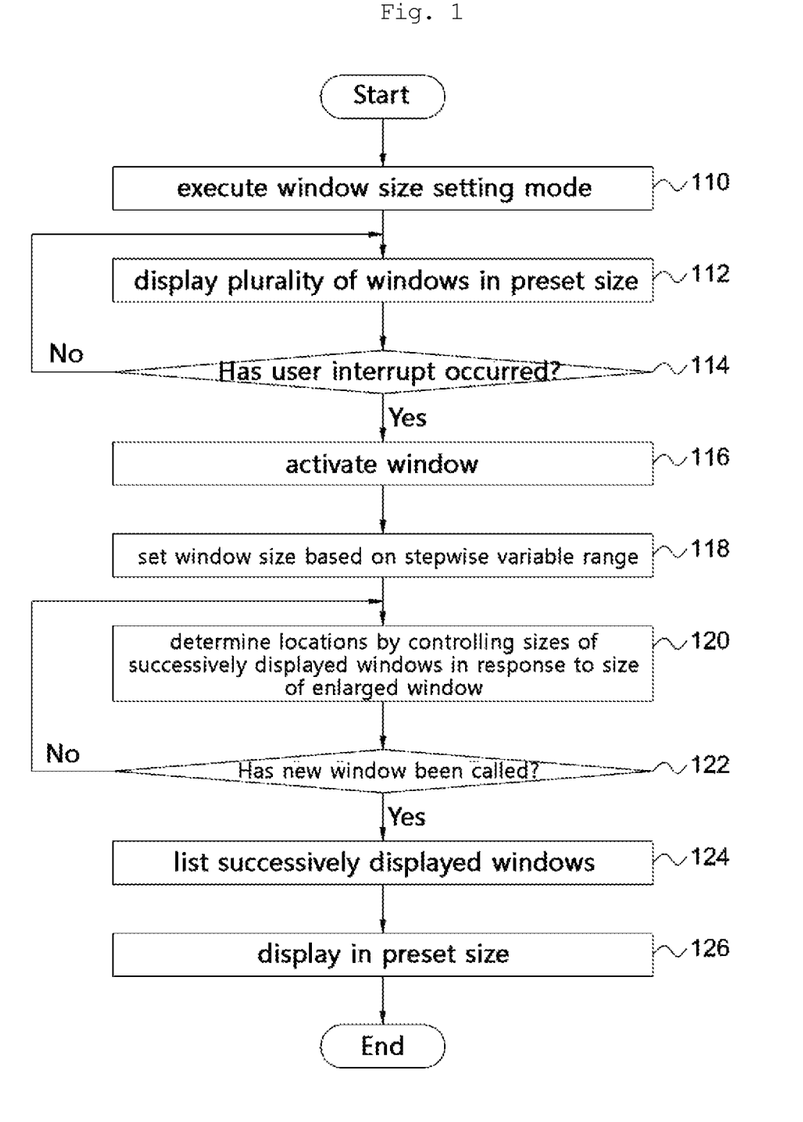
FIG. 1 is an overall flowchart of a method of controlling an EMR system-based output window according to an embodiment of the present invention.

First, FIG. 1 is an overall flowchart of a method of controlling an EMR system-based output window according to an embodiment of the present invention.

Referring to FIG. 1, at step 110, a window size setting mode configured to set sizes for respective windows displayed on an EMR screen is executed.

Once the window size setting mode has been executed, a plurality of windows is successively displayed in a preset size at step 112.

The EMR screen is provided via an EMR service system server, and is configured such that a plurality of menu items is displayed in a preset region and output data corresponding to at least two menu items selected by the user is generated and displayed within a unit window in a preset size on one side of the preset region in which the menu items have been displayed. The applied EMR screen of the present invention is an interface specialized for an EMR service search environment in which all the search data items provided via the EMR service system server are classified and displayed for respective preset regions based on a preset menu bar, a period-based event timeline corresponding to a specific data item selected by the user is displayed below the menu bar, and detailed retrieval items for the data items displayed on the menu bar are classified and displayed for respective search data types on one side of one side of the screen. The plurality of windows is successively displayed in the same size below the portion where the event timeline has been displayed.

At step 114, it is checked whether a user interrupt has occurred for each of the plurality of windows. When a user interrupt has occurred for any one of the displayed windows, the process proceeds to step 116, where the corresponding window is activated. Then at step 118, a window size is set for the activated window based on a stepwise variable range.

At step 120, locations are determined by controlling the sizes of the respective windows successively displayed on the EMR screen in response to the size of the window enlarged based on the stepwise variable range.

Figure 2:
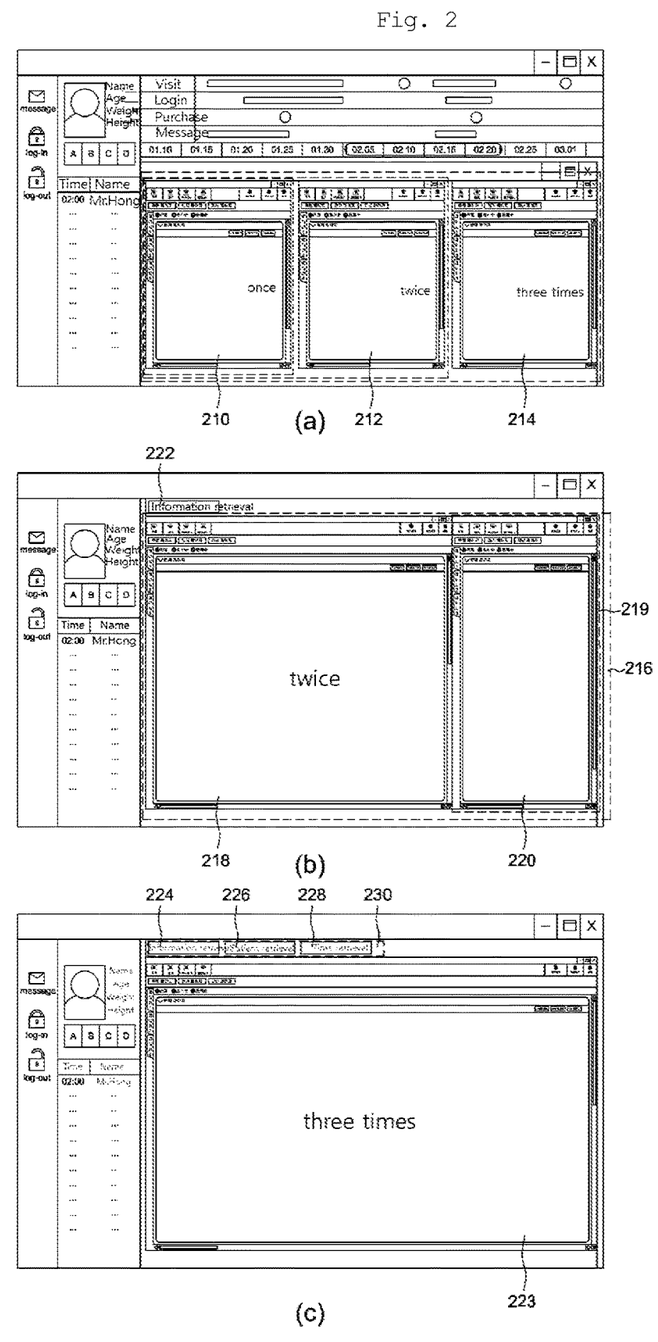
FIG. 2 is an exemplary screen diagram showing the enlargement of a unit window in a method of controlling an EMR system-based output window according to an embodiment of the present invention.

In this case, the stepwise variable range refers to a range within which a unit window of the preset size is enlarged two or three times. As shown in FIG. 2(a), the unit window 210 of the preset size is activated via a user interrupt, and the window 210 of the preset size is enlarged two (see 212) or three times (see 214) in response to a user gesture (for example, a drag that is performed using a user input means).

In this case, the corresponding locations of the remaining windows successively displayed on the EMR screen upon the execution of the window size setting mode, other than the enlarged window, are determined based on the size of the enlarged window.

For example, when the unit window of the preset size is enlarged twice, any one of the displayed unit windows is displayed in a preset size at a location neighboring the window enlarged twice, and the remaining windows are listed in a region in which at least two window titles have been listed.

In greater detail, referring to FIG. 2(b), a case where when a window size setting mode is executed on the EMR screen, the number of displayed windows is 3 is considered. When a first window has been enlarged twice in a preset window display area 216 in response to the selection of a user, as shown in FIG. 2(b), a second window 220 neighboring the first window 218 moves to a third window region 219 in response to the enlargement of the first window 218, and a third window 222 displayed in the third window region 219 is converted into a minimum unit block in the form of a corresponding title, listed, and then located in a predetermined region.

Furthermore, when the first window 223 is enlarged three times, as shown in FIG. 2(c), unit windows (the second window and the third window) displayed in respective regions 226 and 228 are all listed in a region 230 in which at least two window titles have been listed.

In this case, the unit window refers to a window that is displayed on an initial screen when a window size setting mode is executed on the EMR screen and that has a size preset to an original size.

Thereafter, at step 122, it is checked whether a new window, other than the windows initially relayed during the window size setting mode, has been called. If a new window has been called, the process proceeds to step 124, where the windows initially relayed during the window size setting mode are listed and displayed in a predetermined region. Then, at step 126, the called window is displayed in a preset size.

Figure 3:
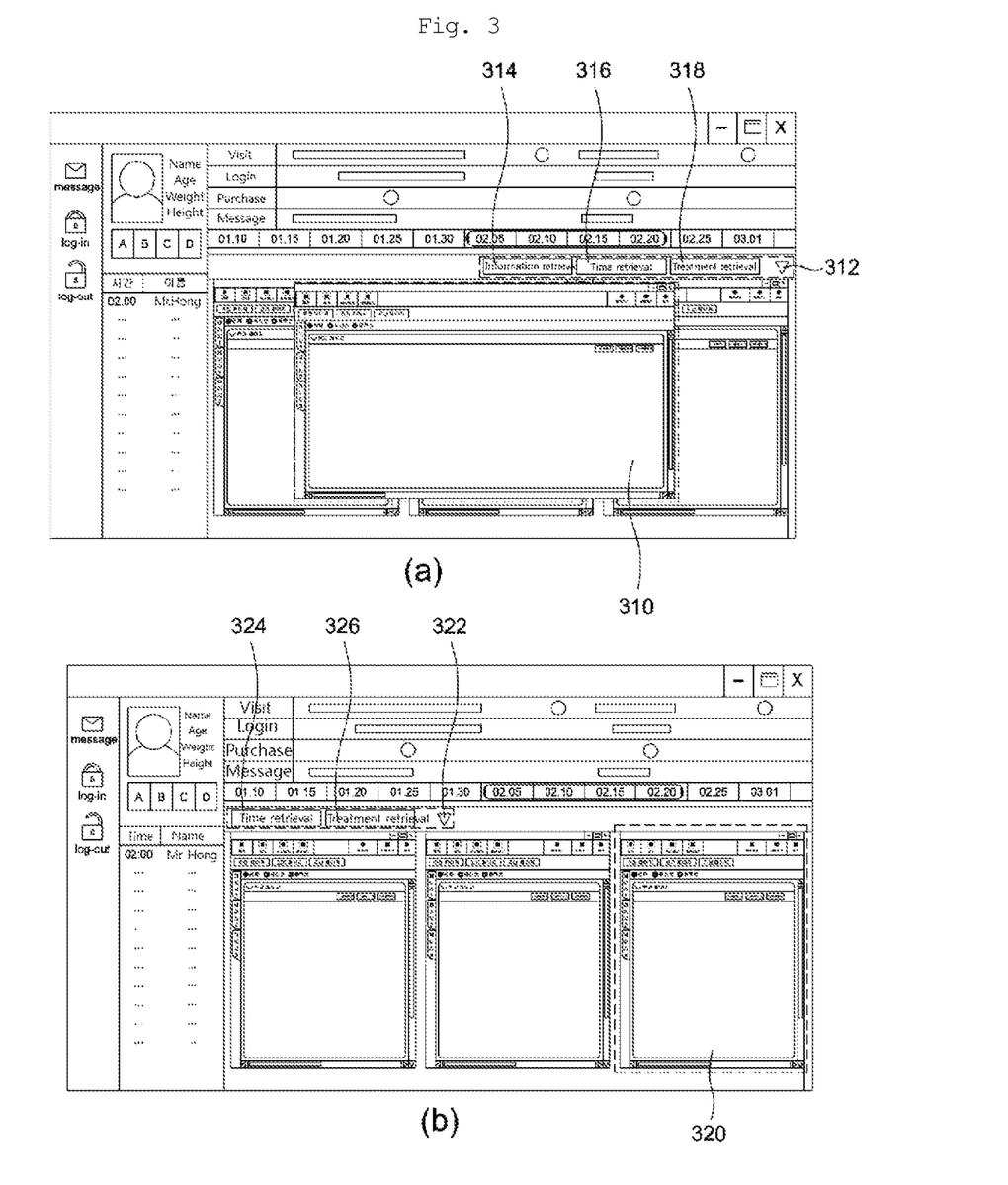
FIG. 3 is an exemplary screen diagram showing the calling of a new window in a method of controlling an EMR system-based output window according to an embodiment of the present invention.

The operations of steps 122 to 126 are now described with reference to FIG. 3(a). If a new window, other than the plurality of windows, i.e., the first, second and third windows, relayed when the window size setting mode was initially executed, has been called by the selection of the user, the corresponding window 310 is displayed in the preset size on the EMR screen, and the displayed first, second and third windows are converted into minimum unit blocks 314, 316 and 318 in the form of corresponding titles and listed in the predetermined region 312. That is, the first, second and third windows 314, 316 and 318 converted into the minimum unit blocks 314, 316 and 318 in the form of corresponding titles and listed are the windows that were relayed onto the corresponding region in the preset size when the window size setting mode was initially executed.

In this case, when the user selects a predetermined one of the windows 324 and 326 listed in the predetermined region 322, the window selected by the user is inserted into the specific region 320 (the third window region when the window size setting mode was initially executed) in response to a user gesture, the window (the third window) displayed in the specific region 320 is listed in the region 322 in which at least two window titles have been listed.

Figure 4:
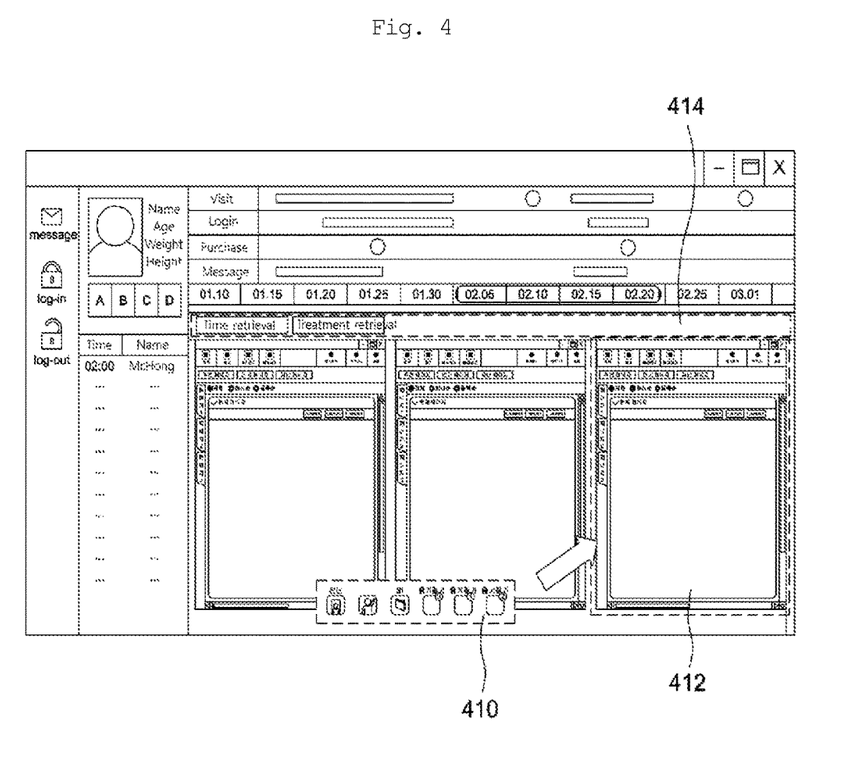
FIG. 4 is an exemplary screen diagram showing an output window representation of service content bookmarked in a bookmark folder in a method of controlling an EMR system-based output window according to an embodiment of the present invention.

FIG. 4 is an exemplary screen diagram showing an output window representation of service content bookmarked in a bookmark folder in a method of controlling an EMR system-based output window according to an embodiment of the present invention.

Referring to FIG. 4, when a bookmark folder 410, in which menu service content has been bookmarked, stored in "my page" registered in an EMR service system and assigned to each user is called, the called bookmark folder 410 is displayed in one region of the EMR screen, and the attribute of the corresponding menu service content of the bookmarked menu service content for which a user interrupt has occurred is detected. If, as a result of the detection, the attribute corresponds to output data that is served within a window, a window is generated in a preset size, and is inserted into and displayed in a preset region 412.

In this case, the window (the third window) displayed in the region 412 into which the generated window is inserted is raised and listed in a region 414 in which at least two window titles have been listed.

Figure 5:
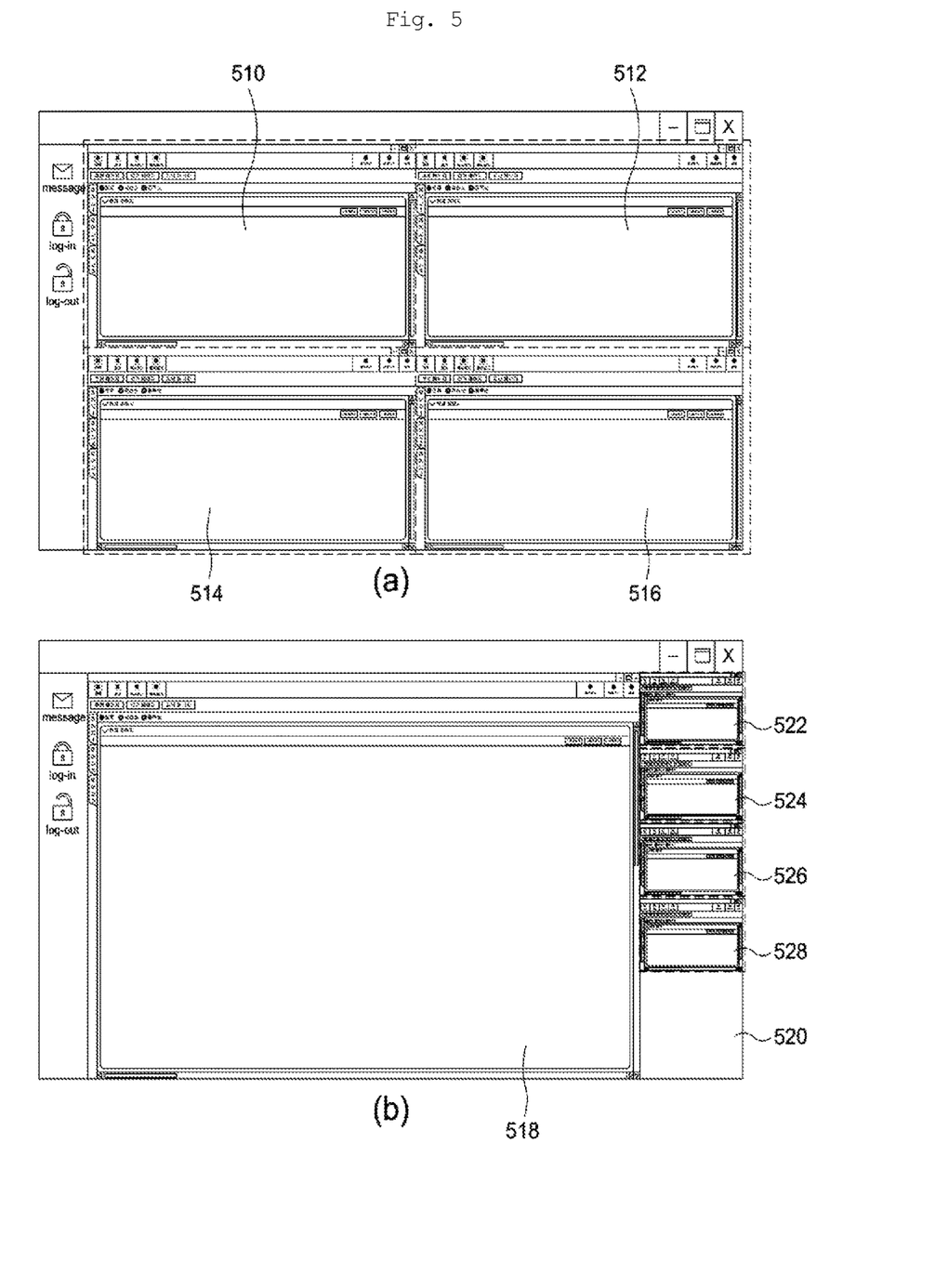
FIG. 5 is an exemplary screen diagram showing an output window representation of an item supported by a specific service function in a method of controlling an EMR system-based output window according to an embodiment of the present invention.

FIG. 5 is an exemplary screen diagram showing an output window representation of an item supported by a specific service function in a method of controlling an EMR system-based output window according to an embodiment of the present invention.

Referring to FIG. 5(a), a plurality of item lists within a specific service function supported by the EMR system is grouped into a preset number.

In the present invention, the individual items are grouped based on quarterly segmentation, segment blocks 510, 512, 514 and 516 are generated in a preset size in accordance with the respective groups of items, and the blocks 510, 512, 514 and 516 in which the individual items are displayed are displayed on the EMR screen.

In this case, when another item, other than the items grouped and displayed in the segment block regions, is called, the called item is displayed in a preset size at a first location 518, as shown in FIG. 5(b), the size of the previously grouped item-based blocks 510, 512, 514 and 516 is reduced on the EMR screen in accordance with the preset size of the called item, and the blocks 510, 512, 514 and 516 are sequentially arranged at another location 520 neighboring the first location 518 (see 522, 524, 526 and 528).

Furthermore, a corresponding segment block is maximized via the pointing of the user to a predetermined region within any one of the segment block regions in which the respective items have been displayed, and the remaining segment blocks, other than the maximized segment block, are reduced to a preset size and arranged on one side of a region in which the maximized segment block is displayed.

In the case where a predetermined block needs to be moved to a neighboring block region on the EMR screen in which the grouped items have been displayed in the respective segment block regions, when the block of the neighboring block region is a block corresponding to a first location block region on the current EMR screen, a block is moved to the first location block region, blocks corresponding to block regions subsequent to the target block are sequentially moved to previous block regions, and then a block displayed in the first location block region is deleted.

The method of controlling an EMR system-based output window according to the embodiment of the present invention has been described above.

An apparatus for controlling an EMR system-based output window according to an embodiment of the present invention is described in detail below with reference to FIG. 6.

Figure 6:
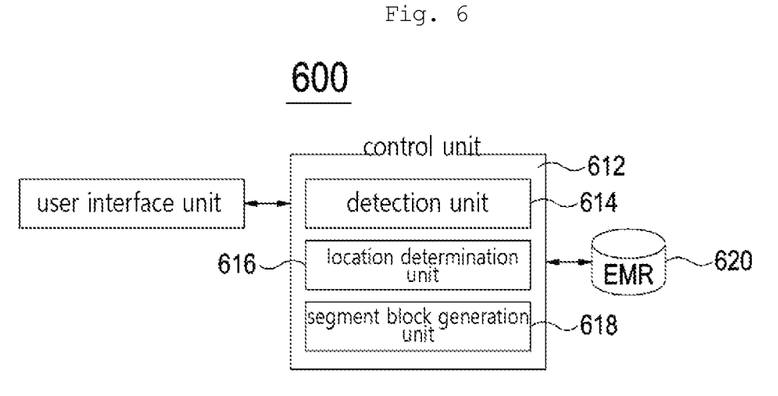
FIG. 6 is a detailed block diagram of an apparatus for controlling an EMR system-based output window according to an embodiment of the present invention.

FIG. 6 is a detailed block diagram of the apparatus for controlling an EMR system-based output window according to the embodiment of the present invention.

Referring to FIG. 6, an apparatus for controlling an EMR system-based output window 600 to which the present invention has been applied includes a user interface unit 610 and a control unit 612.

The user interface unit 610 receives a user interrupt and a user gesture.

The control unit 612 successively displays a plurality of windows in a preset size on an EMR screen according to a window size setting mode; when a user interrupt has occurred for any one of the displayed windows, activates the corresponding window, enlarges the size of the window based on a stepwise variable range for an output window, and determines locations by controlling the sizes of the other successively displayed windows in response to the size of the enlarged window; and when a new window is called, lists the successively displayed windows, displays the listed windows in a predetermined region, and displays the called window in a preset size.

The control unit 612 includes a detection unit 614 configured to identify a window, for which a user interrupt and gesture have occurred, on the EMR screen on which the plurality of windows has been displayed; and a location determination unit 616 configured to perform window-based size control and listing or perform insertion into a specific region in response to a detection signal from the detection unit.

Furthermore, the control unit 612 includes a segment block generation unit 618 configured to group the items of a list, within a specific service function supported by the EMR service system 620, into a preset number of groups, to display segment blocks in accordance with the respective grouped items, to display the items in the respective blocks, and to, when an item, other than the items grouped and displayed in respective segment block regions, is called, display the called item in a segment block region at a first location, sequentially display the item displayed in the segment block region at the first location and items displayed at locations different from the segment block region at the first location in subsequent adjacent segment block regions, and delete an item displayed in a segment block region that is lowest in sequence.

As described above, the operations of the apparatus and method for controlling an EMR system-based output window according to the present invention may be performed. Meanwhile, although the specific embodiments have been described in the description of the present invention, various modifications may be made without departing from the scope of the present invention. Accordingly, the scope of the present invention should not be defined based on the described embodiments, but should be defined based on the claims and equivalents thereto.

The invention claimed is:

1. A method of controlling an Electronic Medical Record (EMR) system-based output window, comprising:
   when a window size setting mode configured to set sizes for respective windows displayed on an EMR screen is executed, successively displaying a plurality of windows in a preset size;
   when a user interrupt has occurred for any one of the displayed windows, activating the corresponding window, and enlarging a size of the window based on a stepwise variable range for an output window;
   determining locations by controlling sizes of the respective windows successively displayed on the EMR screen in response to the size of the window enlarged based on the stepwise variable range;
   when a window different from the windows successively displayed upon the window size setting mode is called, listing the successively displayed windows, displaying the listed windows in a predetermined region, and displaying the called window in a preset size;
   calling a bookmark folder, in which menu service content has been bookmarked, stored in "my page" registered in an EMR service system and assigned to each user;
   displaying the called bookmark folder within the EMR screen, and detecting an attribute of corresponding menu service content of the bookmarked menu service content for which a user interrupt has occurred;
   if, as a result of the detection, the attribute corresponds to output data that is served within a window, generating a window in a preset size, and inserting the generated window into a preset region; and
   listing the window, displayed in the region into which the generated window is inserted, in a region in which at least two window titles have been listed.

2. The method of claim 1, further comprising inserting a window selected from the listed windows into a specific region in response to a user gesture, and listing the window displayed in the specific region in a region in which at least two window titles have been listed.

3. The method of claim 1, further comprising:
   grouping items of a list, within a specific service function supported by an EMR service system, into a preset number of groups;
   generating segment blocks in accordance with the respective grouped items, and displaying the items in the respective blocks;
   when an item, other than the items grouped and displayed in respective segment block regions, is called, displaying the called item in a segment block region at a first location; and
   sequentially display item blocks displayed in the segment block region at the first location in adjacent regions on an itemized basis;
   wherein, after the items have been displayed in the respective blocks, when a predetermined block needs to be moved to a neighboring block region, blocks displayed in the target block region are sequentially displayed in block regions sequentially previous to the target block region if there are the sequentially previous block regions, deletion is performed if there are no sequentially previous block regions, and blocks sequentially subsequent to the movement target block region are sequentially moved to and displayed in neighboring block regions.

4. The method of claim 3, further comprising maximizing a corresponding segment block via pointing of the user to a predetermined region within any one of the segment block regions in which the respective items have been displayed, reducing the remaining segment blocks, other than the maximized segment block, to a preset size, and arranging the reduced remaining segment blocks on one side of a region in which the maximized segment block is displayed.

5. The method of claim 1, wherein the stepwise variable range refers to a range within which a unit window of the preset size is enlarged two or three times; when the unit window of the preset size is enlarged twice, any one of the displayed unit windows is displayed in a preset size at a location neighboring the window enlarged twice, and the remaining windows are listed in a region in which at least two window titles have been listed; and when the unit window is enlarged three times, the displayed unit windows are all listed in a region in which at least two window titles have been listed.

6. The method of claim 1, wherein the EMR screen is provided via an EMR service server, and is configured such that a plurality of menu items is displayed in a preset region and output data corresponding to at least two menu items selected by the user is generated and displayed within a unit window in a preset size on one side of the preset region in which the menu items have been displayed.

7. An apparatus for controlling an EMR system-based output window, comprising:
a user interface unit configured to receive a user interrupt and a user gesture; and
a controller configured to:
successively display a plurality of windows in a preset size on an EMR screen according to a window size setting mode,
when a user interrupt has occurred for any one of the displayed windows, activate the corresponding window, and enlarge a size of the window based on a stepwise variable range for an output window,
determine locations by controlling sizes of the other successively displayed windows in response to the size of the enlarged window;
when a new window is called, list the successively displayed windows, display the listed windows in a predetermined region, and display the called window in a preset size;
call a bookmark folder, in which menu service content has been bookmarked, stored in "my page" registered in an EMR service system and assigned to each user;
display the called bookmark folder within the EMR screen, and detecting an attribute of corresponding menu service content of the bookmarked menu service content for which a user interrupt has occurred;
if, as a result of the detection, the attribute corresponds to output data that is served within a window, generate a window in a preset size, and inserting the generated window into a preset region; and
list the window, displayed in the region into which the generated window is inserted, in a region in which at least two window titles have been listed.

8. The apparatus of claim 7, wherein the controller comprises:
a detection unit configured to identify a window, for which a user interrupt and gesture have occurred, on the EMR screen on which the plurality of windows has been displayed; and
a location determination unit configured to perform window-based size control and listing or perform insertion into a specific region in response to a detection signal from the detection unit.

9. The apparatus of claim 7, wherein the controller further comprises:
a segment block generation unit configured to group items of a list, within a specific service function supported by an EMR service system, into a preset number of groups, to display segment blocks in accordance with the respective grouped items, to display the items in the respective blocks, and to, when an item, other than the items grouped and displayed in respective segment block regions, is called, display the called item in a segment block region at a first location, sequentially display the item displayed in the segment block region at the first location and items displayed at locations different from the segment block region at the first location in subsequent adjacent segment block regions, and delete an item displayed in a segment block region that is lowest in sequence.

* * * * *